United States Patent
Hines

(10) Patent No.: US 9,121,754 B2
(45) Date of Patent: Sep. 1, 2015

(54) SURFACE ACOUSTIC WAVE MONITOR FOR DEPOSITION AND ANALYSIS OF ULTRA-THIN FILMS

(75) Inventor: Jacqueline H. Hines, Arnold, MD (US)

(73) Assignee: SenSanna Incorporated, Arnold, MD (US)

(*) Notice: Subject to any disclaimer, the term of this patent is extended or adjusted under 35 U.S.C. 154(b) by 502 days.

(21) Appl. No.: 13/485,317

(22) Filed: May 31, 2012

(65) Prior Publication Data

US 2014/0007692 A1   Jan. 9, 2014

Related U.S. Application Data

(60) Provisional application No. 61/512,908, filed on Jul. 28, 2011.

(51) Int. Cl.
| | |
|---|---|
| *H03H 9/25* | (2006.01) |
| *G01H 11/08* | (2006.01) |
| *H03H 9/205* | (2006.01) |
| *G01N 29/02* | (2006.01) |
| *G01N 29/036* | (2006.01) |
| *G01N 29/12* | (2006.01) |
| *G01N 29/24* | (2006.01) |
| *C23C 14/54* | (2006.01) |

(52) U.S. Cl.
CPC ............. *G01H 11/08* (2013.01); *C23C 14/546* (2013.01); *G01N 29/022* (2013.01); *G01N 29/036* (2013.01); *G01N 29/12* (2013.01); *G01N 29/2462* (2013.01); *H03H 9/205* (2013.01); *G01N 2291/0256* (2013.01); *G01N 2291/0422* (2013.01); *G01N 2291/0423* (2013.01)

(58) Field of Classification Search
CPC .................................................. G01N 29/022
USPC ........... 310/313 R, 313 B, 318, 340; 333/193
See application file for complete search history.

(56) References Cited

U.S. PATENT DOCUMENTS

| | | | | |
|---|---|---|---|---|
| 3,582,540 | A | * | 6/1971 | Adler et al. .................... 348/507 |
| 3,596,211 | A | * | 7/1971 | Dias et al. ..................... 333/194 |
| 3,810,257 | A | * | 5/1974 | Jones et al. .................... 333/151 |
| 3,908,137 | A | * | 9/1975 | Hunsinger et al. ......... 310/313 D |
| 3,962,652 | A | * | 6/1976 | Zarin et al. .................... 331/1 R |
| 4,037,175 | A | * | 7/1977 | Kansy et al. ................... 333/152 |

(Continued)

OTHER PUBLICATIONS

Pohl, A., et al., "Notch Sensors—A New Signal Processing Method for Interrogation of Passive SAW Sensors", 1997 IEEE Ultrasonics Symposium, Oct. 5-8, 1997, pp. 355-358, vol. 1.

*Primary Examiner* — Thomas Dougherty
(74) *Attorney, Agent, or Firm* — Nixon Peabody LLP; Jeffrey L. Costellia

(57) ABSTRACT

A surface acoustic wave (SAW) based thin film deposition monitor device and system for monitoring the deposition of ultra-thin films and nanomaterials and the analysis thereof is characterized by acoustic wave device embodiments that include differential delay line device designs, and which can optionally have integral reference devices fabricated on the same substrate as the sensing device, or on a separate device in thermal contact with the film monitoring/analysis device, in order to provide inherently temperature compensated measurements. These deposition monitor and analysis devices can include inherent temperature compensation, higher sensitivity to surface interactions than quartz crystal microbalance (QCM) devices, and the ability to operate at extreme temperatures.

27 Claims, 11 Drawing Sheets

(56) References Cited

U.S. PATENT DOCUMENTS

| | | | | |
|---|---|---|---|---|
| 4,237,432 A | * | 12/1980 | Huang et al. | 333/194 |
| 5,163,435 A | * | 11/1992 | Soldner et al. | 600/447 |
| 6,331,747 B2 | * | 12/2001 | Yoshida et al. | 310/313 R |
| 8,441,168 B2 | * | 5/2013 | Hines et al. | 310/313 R |
| 2014/0001918 A1 | * | 1/2014 | Lee et al. | 310/313 B |

* cited by examiner (a)

(b)

SURFACE ACOUSTIC WAVE MONITOR FOR DEPOSITION AND ANALYSIS OF ULTRA-THIN FILMS

CROSS-REFERENCE TO RELATED APPLICATIONS

This application claims the benefit of U.S. Provisional Application No. 61/512,908, filed Jul. 28, 2011, herein incorporated by reference in its entirety.

STATEMENT REGARDING FEDERALLY SPONSORED RESEARCH OR DEVELOPMENT

This invention was made with government support under contract NNX10CD41P awarded by the National Aeronautics and Space Administration (NASA). The government has certain rights in the invention.

BACKGROUND OF THE INVENTION

1. Field of the Invention

The present invention relates to thin film deposition monitoring and analysis of thin films, and in particular, to apparatus, systems, devices, and methods for monitoring the deposition of ultra-thin films and nanomaterials, and analyzing the properties thereof using surface acoustic wave technology.

2. Description of Related Art

Thin films are deposited by many means, including but not limited to evaporation (thermal or e-beam), sputtering (DC or RF), chemical vapor deposition (CVD), plasma enhanced chemical vapor deposition (PECVD), laser assisted deposition, atomic layer deposition (ALD), and others. The most appropriate technique with which to deposit a film depends on characteristics of the particular film, including composition, electrical conductivity, thermal behavior, physical properties (such as melting point), etc. Films can be relatively thick (microns), or as thin as an atomic layer, can be continuous or discontinuous, and can have properties characteristic of the bulk material deposited, or can have widely different properties, including but not limited to nanostructures and nanomaterial based properties. In almost all cases, the thickness and other properties of the film such as conductivity, viscoelastic properties, and others are important to the ultimate function of the film. Having a real-time deposition monitor capable of monitoring deposition rate, and monitoring properties of the films during deposition and after deposition is complete, is beneficial for process control and optimization of such deposition processes. This has been recognized for decades, and much literature exists related to different ways to implement thing film deposition monitors, although historically this work has focused on "thin" films in the thickness range of microns. It is only relatively recently that the need has emerged for monitoring ultra-thin and nanostructured material deposition.

Widespread commercial application of nanomaterials has been hindered by a lack of measurement techniques capable of providing information on material quality and uniformity for use in manufacturing process control. This is true for a range of promising nanomaterials, from nanocluster metal films to molecularly imprinted polymers, and especially carbon nanotubes. Carbon nanotubes have unique thermal, electrical, and physical properties that make them well suited to many applications, including conductive and high-strength composites, nanometer sized electronics, energy storage, energy conversion, hydrogen storage, and field emission devices such as flat panel displays. R. H. Baughman, A. A. Zakhidov, W. A. de Heer, "Carbon Nanotubes—the Route Toward Applications", *Science*, Vol 297, 2 Aug. 2002, 787-792. While specific commercial applications have been realized, particularly for multiwalled nanotubes (MWNTs) which have been used as electrically conductive additives in polymers and plastics since the early 1990s, manufacturing issues such as polydispersity in nanotube type, impurities, and high cost for high purity single wall nanotubes (SWNTs) limit the widespread adoption of this potentially beneficial technology.

The commercial potential for deposition monitor devices that are the subject of embodiments of the invention is therefore related to the commercial potential for nanomaterials, the most promising of which are single walled and multiwalled carbon nanotubes. A brief description of selected current and potential applications is included below.

Multiwalled carbon nanotubes have been commercially utilized in significant quantities as electrically conductive additives to plastics and polymers since the early 1990s, an application that is tolerant of MWNTs with relatively high defect densities. R. H. Baughman, A. A. Zakhidov, W. A. de Heer, "Carbon Nanotubes—the Route Toward Applications", *Science*, Vol 297, 2 Aug. 2002, 787-792. Commercial automotive gas lines and filters use fillers with conductive MWNTs that dissipate the static charge buildup that could lead to explosions. SWNTs and MWNTs also appear promising as additives to plastics for enhanced strength and thermal conductivity. The high electrochemically accessible surface area of CNT arrays combined with their electrical conduction properties make them promising materials for use in high capacity "supercapacitors", which could find widespread use in hybrid vehicles. R. H. Baughman, A. A. Zakhidov, W. A. de Heer, "Carbon Nanotubes—the Route Toward Applications", *Science*, Vol 297, 2 Aug. 2002, 787-792. Nanotube actuators operate at voltages one to two orders of magnitude lower than piezoelectric or electrostrictive actuators, making them promising for low power applications (and reduction in power consumption for any application). R. H. Baughman, A. A. Zakhidov, W. A. de Heer, "Carbon Nanotubes—the Route Toward Applications", *Science*, Vol 297, 2 Aug. 2002, 787-792. Field emission devices are another very promising CNT application, particularly for flat panel displays, an area actively being developed by industry. The commercial competitiveness of these displays, which can potentially have higher brightness, lower power consumption, faster response rate, and wider viewing angle than other current display technologies, will depend on the successful development of electronic technologies needed for addressing, and on concurrent advances in competitive display technologies such as LCD and non-CNT LED displays. R. H. Baughman, A. A. Zakhidov, W. A. de Heer, "Carbon Nanotubes—the Route Toward Applications", *Science*, Vol 297, 2 Aug. 2002, 787-792.

Silicon based electronics have become smaller and smaller over the past few decades, producing faster processors with increased computational power. This size reduction process, however, is fundamentally limited by the physical and electrical properties of the materials being used. Carbon nanotubes are extremely promising for use in nanometer-sized electronics, allowing smaller devices with better thermal (power handling) properties and faster computational speeds. IBM has been a pioneer in developing these devices, demonstrating arrays of CNT based transistors in 2001 (*Science*, Vol 292, Issue 5517, Apr. 27, 2001), and logic devices with CNTs shortly thereafter (*Nanoletters*, Aug. 26, 2001 Web edition).

Hydrogen storage in nanotubes is another potential use, although their promise is not as clear for this as it is for other applications. R. H. Baughman, A. A. Zakhidov, W. A. de Heer, "Carbon Nanotubes—the Route Toward Applications", *Science*, Vol 297, 2 Aug. 2002, 787-792.

Widespread adoption of CNTs for these and other applications has been hindered by manufacturing issues, including difficulty in obtaining homogeneous samples of one type of CNT, and impurities resulting from the manufacturing process. These issues are more significant for applications that will not tolerate high defect densities, such as nanoscale electronics, and result in higher costs for high purity NT materials. While costs have dropped greatly in the past decade, further cost reductions, particularly for high purity SWNTs, will be needed for adoption in certain commercial applications. The deposition monitor technology that is the subject of embodiments of the present invention will provide a manufacturing process monitoring and quality control tool, allowing for thermal decomposition studies of CNT batch samples, evaluation of CNT physical and electrical properties, and potentially real-time monitoring of CNT formation within growth systems. Such a tool would enhance CNT manufacturing capabilities, reducing product costs and accelerating adoption of these promising materials in a plethora of applications.

In order to provide an understanding of the aspects of the devices and systems described in embodiments of the present invention, it is necessary to first discuss conventional film deposition monitors, and specifically quartz crystal microbalance (QCM) technology and its drawbacks related to the use of QCM devices to monitoring deposition of ultra-thin films.

Deposition Monitors:

Conventional film deposition monitors include acoustic, optical, and impedance-based techniques. Acoustic techniques include QCM, thin film bulk acoustic resonator (FBAR), and SAW approaches. Each of these areas is discussed below. Optical techniques include optical absorption or attenuation, optical reflection, and optical fiber techniques. Impedance-based techniques include measurement of film conductivity based on step coverage, and others.

QCM Deposition Monitors:

Quartz crystal microbalance (QCM) devices rely on a thickness shear resonant condition in a bulk crystal (usually AT-quartz), the frequency of which is changed by the deposition of materials on the device surface. These devices were first investigated almost 50 years ago, and it is well known that for rigidly adhered acoustically thin films, the change (reduction) in frequency of resonance caused by addition of the film is proportional to the added film mass multiplied by the square of the resonant frequency of the QCM (M. Thompson and D. C. Stone, *Surface-Launched Acoustic Wave Sensors*, John Wiley & Sons Inc., NY, 1997), while the low electromechanical coupling coefficient of quartz means that film electrical properties do not impact device response. This simple relationship has made the QCM a very useful tool in the manufacturing of thin films of many kinds over the past few decades. Metal, dielectric, and other film deposition systems used in the manufacture of electronic components generally utilize QCM film thickness monitors to ensure proper film deposition rates and thicknesses. Systems such as electron beam deposition, sputtering, and chemical vapor deposition can all make use of this technology to monitor film deposition conditions. Typical commercial deposition monitors claim resolutions that are on the order of 1-2 angstroms for film thicknesses of 1000 angstroms or less. However, deposition of ultrathin films (under 50 angstroms thick) and nanostructured materials present particular challenges, and QCM devices are of limited usefulness for monitoring the deposition of these materials. The sensitivity of the QCM to thermal transients when the shutter is opened in an e-beam system, for example, may result in slight errors in the reported deposition rate and film thickness. For nanostructured films, such errors can result in film morphologies that differ widely from the desired films. In addition, deposition of multiple films can easily push the device into a regime of lower sensitivity as the overall film thickness increases. In addition to monitoring film deposition, QCM devices have (in the past) achieved widespread use as a method for monitoring molecular contamination of surfaces in manufacturing and clean room applications (these applications have since transitioned to surface acoustic wave (SAW) monitors due to enhanced sensitivities).

Recently, QCM devices have been used as a tool to characterize nanomaterials such as carbon nanotubes, and for molecular and biological imprinting and sensing research. Drop-casting of solutions containing carbon nanotubes onto QCMs has been studied by researchers at the University of Maryland Baltimore County (UMBC) and the National Institute of Standards and Technology (NIST). S. Hooker, A. Kar, and R. Schilt, "Evaluation of Quartz Crystal Microbalance Thermal Analysis in Characterization of Carbon Nanotube Purity", Poster session, $3^{rd}$ NASA-NIST Workshop on Nanotube Measurements, September 26-28, NIST, Gaithersburg Md.; H. Wilson, S. Hooker, and A. Kar, "Purity of Carbon Nanotubes: Separating the Nanotube from the Dispersant in Thermal Decomposition Profiles", Poster session, $3^{rd}$ NASA-NIST Workshop on Nanotube Measurements, September 26-28, NIST, Gaithersburg Md. These studies have shown promising results for using the QCM devices to evaluate sample homogeneity, and to study the thermal decomposition properties of the CNT samples. Molecular imprinting has been studied as a means to produce sensor materials selective for both molecular analytes and biological moieties such as cells and microorganisms. QCM devices have been useful tools for measurement of such sensor films. P. A. Lieberzeit, G. Glanzing, M. Jenik, S. Gazda-Miarecka, F. L. Dickert, and A. Leidl, "Softlithography in Chemical Sensing—Analytes from Molecules to Cells", *Sensors* 2005, 5, 509-518; M. Penza et. al, "Carbon nanotubes-coated multi-transducing sensors for VOCs detection", *Sensors and Actuators B: Chemical*, Vol. 111-112, 11 Nov. 2005, 171-180; H. Chen et. al., "The application of CNT/Nafion composite material to low humidity sensing measurement", *Sensors and Actuators B: Chemical*, Vol. 104, 3 Jan. 2005, 80-84; M. Consales et. al., "Carbon nanotubes thin films fiber optic and acoustic VOCs sensors: Performance analysis", *Sensors and Actuators B: Chemical*, Vol. 118, 25 Oct. 2006, 232-242. Dissipation monitoring of QCM devices (QCM-D) utilizes these devices in a dynamic mode—the drive energy to the QCM is switched off, and the decay of the damped oscillation is measured. This technique can be used to provide additional information about adhered layers, and has been applied primarily in polymeric and biological research. A. Jaiswal, "In-Situ Characterization of Polymer Layer Formation by Quartz Crystal Microbalance with Dissipation Monitoring (QCM-D)", Nanotech 2007 Conference.

The QCM devices discussed generally operate in the low MHz range—often 5 MHz to 15 MHz. These devices are limited to low frequency operation because the crystal substrate thickness determines the operating frequency, and higher frequencies would require very thin, fragile crystals. Theoretical mass detection limits of typical QCM devices are generally in the $10^{-12}$ gram (picogram) range. M. Thompson and D. C. Stone, *Surface-Launched Acoustic Wave Sensors*, John Wiley & Sons Inc., NY, 1997.

QCM TGA Monitors:

Recently, quartz crystal microbalance (QCM) devices have been utilized as a measurement platform to perform microscale thermogravimetric analysis (TGA) of nanoparticles, thin films, and other materials. Mansfield, E. et. al., "Quartz Crystal Microbalances for Microscale Thermogravimetric Analysis", *Anal. Chem.* 2010, 82, 9977-9982; Mansfield, E. et. al., "Applications of TGA in quality control of SWCNTs", *Anal Bioanal Chem* (2010) 396:1071-1077. This approach has the benefit of requiring only micrograms of sample, compared to several milligrams of sample required by conventional TGA techniques. This work has shown that QCM-based TGA can provide a 3-fold increase in resolution compared to the state-of-the-art using standard TGA techniques. Mansfield, E. et. al., "Quartz Crystal Microbalances for Microscale Thermogravimetric Analysis", *Anal. Chem.* 2010, 82, 9977-9982. However, the cited work performed measurements in a batch type operation, where QCM crystals with samples were measured, removed from their fixtures for heating to a pre-selected temperature and cooling, and then re-inserted into their fixtures for subsequent measurement of the QCM.

Embodiments of the present invention provide significant improvements over this type of QCM, in that real-time in-situ measurements can be made as temperature varies to provide immediate feedback on reaction kinetics and sample properties as the sample is heated and cooled.

FBAR Deposition Monitors:

Film bulk acoustic resonators (FBARs) are acoustic resonant devices produced by layering materials with differing acoustic properties to form an acoustic cavity structure suitable to sustain resonance at a particular frequency. FBAR devices have been used by Larson as film deposition monitors. Larson, J. D., et. al., "Systems and methods of monitoring thin film deposition", U.S. Pat. No. 6,668,618, 2003. In this example, as in the SAW application discussed below and in Hemphill, R. B., "A surface wave thickness monitor for thin evaporated films", *Proceedings of the IEEE International Ultrasonics Symposium*, p. 525-529, 1984, a reference acoustic device of the same type (FBAR or SAW) that is shielded from deposition of the film being deposited is used to provide a reference response during deposition. This reference device can be thermally coupled to the acoustic device exposed to film deposition, allowing unambiguous separation of film thickness and thermal effects.

SAW Deposition Monitors:

Since 1979, surface acoustic wave (SAW) devices have been recognized as a promising alternative to QCMs for sensing applications requiring higher sensitivity and lower detection limits. H. Wohltjen and R. Dessey, *Anal. Chem.,* 1979, 51, 1458, 1465. The ability of SAW devices to perform as an analytical tool to evaluate changes in the properties of deposited films was also recognized some time ago, as in Wohltjen's work on thin film polymer characterization. H. Wohltjen and R. Dessey, *Anal. Chem.,* 1979, 51, 1470. Due to construction of SAW devices, the operating frequency can be set independently of the crystal substrate thickness, by patterning interdigital electrodes on the crystal surface with selected pitch. Typical SAW device operating frequencies range from 50 MHz to 3 GHz. Since the mass sensitivity of these devices is (to first order) proportional to the square of the operating frequency, SAW devices have substantially higher mass sensitivity. In 1984, Wohltjen argued that SAW devices at 3 GHz with active surface areas of $10^{-4}$ cm$^2$ would have a realistic detection limit of roughly $3 \times 10^{-15}$ grams (femtograms), taking into consideration typical measurement system noise. H. Wohltjen, *Sens. Actuators,* 1984, 5, 307. Thus, SAW microbalances are capable of two to three orders of magnitude greater mass sensitivity than QCM devices. Also in 1984, Hemphill published his work on a SAW thickness monitor for thin evaporated films. Hemphill, R. B., "A surface wave thickness monitor for thin evaporated films", *Proceedings of the IEEE International Ultrasonics Symposium*, p. 525-529, 1984. This approach utilized an evaporated shorting layer on the surface of the SAW propagation path to short out the electric field at the surface of the device. This made the monitor insensitive to changes in conductivity of the film being deposited, making it sensitive only to the mass and viscoelastic properties of the film. While useful for certain films, this prevented use of film conductivity as a parameter for deposition monitoring. This work (Hemphill, R. B., "A surface wave thickness monitor for thin evaporated films", *Proceedings of the IEEE International Ultrasonics Symposium*, p. 525-529, 1984) also discusses the use of this device to measure relatively thick films, with thicknesses of up to 100 microns or more.

Molecular contamination monitors adopted SAW microbalances as an improvement over QCM devices several years ago. "Monitoring Molecular Contamination of Critical Surfaces in Semoconductor Manufacturing", *Application Note, Particle Measurement Systems,* 2002, www.pmeasuring.com; D. Rodier, "Method and apparatus for monitoring molecular contamination of critical surfaces", U.S. Pat. No. 6,945,090, 2005, the disclosure of which is herein incorporated by reference in its entirety. These contamination monitors measure the accumulation of contamination on critical surfaces such as silicon dioxide, metals, and polymers relevant to the semiconductor manufacturing clean room environment. Carbon nanotubes have also been used on SAW devices as chemically selective elements for vapor sensing (M. Penza, F. Antolini, and M. V. Antisari, "Carbon nanotubes as SAW chemical sensors materials", *Sensors and Actuators B: Chemical,* Vol. 100, 1 Jun. 2004, 47-59; M. Penza, F. Antolini, and M. V. Antisari, "Carbon nanotubes-based surface acoustic waves oscillating sensor for vapor detection", *Thin Solid Films,* Vol. 472, Issues 1-2, 24 Jan. 2005, 246-252), as have numerous metal oxide and polymer films (M. Thompson and D. C. Stone, *Surface-Launched Acoustic Wave Sensors,* John Wiley & Sons Inc., NY, 1997). In addition to being highly mass sensitive, with acoustic wave velocity changing with deposited mass on the surface, SAW devices respond to changes in other parameters of coating films and fluids in contact with the device surface. Film conductivity will change the SAW propagation velocity and attenuation if a substrate such as lithium niobate (which has a high electromechanical coupling coefficient) is used. Physical film or fluid properties, such as stiffness, elasticity, viscosity, etc. also alter device performance measurably, producing changes in velocity and/or attenuation. Various surface launched acoustic wave propagation modes can be used to generate surface wave devices that will operate in either liquid or gaseous media, and the device can be optimized for the anticipated environment. Finally, SAW devices are extremely rugged and can operate over a very wide temperature range. With colleagues, the inventor is currently developing sensors for NASA applications that require operation at temperatures ranging from cryogenic to almost 1000° C. These devices have thus far been demonstrated to tolerate repeated cycling from cryogenic (liquid nitrogen) temperatures to room temperature, and from room temperature to temperatures in excess of 300° C. This operating temperature range has been demonstrated successfully using both single crystal quartz and lithium niobate substrates. The upper limit on device testing has been limited by our test capability. Fundamentally, the upper limit on operating temperature for quartz devices is limited (to no more than 500-550° C.) by the crystalline α-β phase transition that occurs at 573° C., although traditional quartz devices operate near ambient room temperatures in order to take advantage of the zero first order temperature coefficient of frequency near room temperature. Lithium niobate devices can operate at higher temperatures than quartz, and devices fabricated on langasite, langanite, or langatate can operate up to 1000° C. or more.

SUMMARY OF THE INVENTION

A surface acoustic wave (SAW) based thin film deposition monitor device and system for monitoring the deposition of ultra-thin films and nanomaterials and the analysis thereof is characterized by acoustic wave device embodiments that include differential delay line device designs, and which can optionally have integral reference devices fabricated on the same substrate as the sensing device, or on a separate device in thermal contact with the film monitoring/analysis device, in order to provide inherently temperature compensated measurements. These deposition monitor and analysis devices can include inherent temperature compensation, higher sensitivity to surface interactions than quartz crystal microbalance (QCM) devices, and the ability to operate at extreme temperatures. This device structure will operate to provide real-time information on deposition rate and properties of deposited films for continuous, discontinuous, or partially continuous films of as little as several angstroms thickness, providing a platform useful for characterizing a wide range of ultra-thin films, including nanomaterials such as nanocluster metal films, carbon nanotubes, and other nanostructured materials. A transceiver circuit can be configured to provide wired or wireless interrogation of the deposition monitor and analysis device or group of devices.

Embodiments of the invention comprise novel acoustic wave device embodiments that include differential delay line device designs, and which can optionally have integral reference devices fabricated on the same substrate as the sensing device, or on a separate device in thermal contact with the deposition monitor device, in order to provide inherently temperature compensated measurements. Thus, these devices would be able to operate over a wide range of temperatures without suffering the temperature-induced inaccuracies of current QCM and SAW sensors. Previously described SAW microbalance devices generally use either the resonance frequency of a SAW resonator (measured directly, or as phase, or derived using the Fourier Transform of the amplitude of the sensor impulse response), or the time delay of a SAW delay line as the parameter measured to determine mass loading or sensor response. The deposition monitor device that is the subject of embodiments of the present invention is fundamentally different from any of these approaches in than it utilizes a reflective transversal filter response $S_{11}$ as an indicator of the device mass loading due to the deposited film, as well as the film conductivity, and film viscoelastic properties. As surface mass, conductivity, and viscoelastic film properties of the deposition monitor device change, the reflective transversal filter response shifts or fundamentally changes its nature in both the frequency and time domains. Measurement of the power spectral density of the sensor response provides a sensitive means of determining the device temperature, and the characteristics of the deposited film. The changes can also be observed in (or extracted from) the time domain response. These devices can be designed to respond to film conductivity, allowing measurement of extremely thin (as low as several angstroms) conductive, partially conductive, and semiconducting films. Alternate device configurations can be used to measure viscoelastic properties and/or mass loading of films being deposited. The devices can be modified to detect all of these film properties, or to selectively evaluate one or more property independently of the others. These devices respond in microseconds, making real-time monitoring during deposition feasible. The operating principles of devices according to embodiments of the present invention allow the designer to specify the device sensitivity desired (over a wide range of sensitivities) through the device design, rather than relying only on fundamental material parameters and device geometry to determine device sensitivity. This flexibility, combined with selection of the appropriate acoustic wave mode(s), will enable the deposition monitor devices to be designed to operate in environments ranging from vapors, to solid films, polymer coatings, or drop-cast coatings, and even viscous liquids. Additionally, these devices share the common benefits of SAW technology, including being solid state devices that are small, rugged, and can be produced in quantities at low cost.

In addition to providing deposition monitor devices with sensitivities that are higher than traditional SAW devices (and much higher than QCM devices), and that can be made inherently temperature compensated (thus enabling operation over a wide temperature range), the proposed devices can utilize a simple interrogation system with increased signal to noise levels compared to traditional SAW and QCM oscillator systems. The reflective transversal filter response can be monitored in appropriate frequency ranges by a system that is capable of detecting changes in amplitude, delay, and power spectral density of the response. This system uses the process of time integrating correlation to amplify the desired sensor response relative to background noise. Time integrating correlators are fairly simple, yet are capable of achieving large processing gain, as is well known in the field of signal processing. In the proposed system, it is anticipated that utilizing integration times of 10 milliseconds, processing gains in excess of 63 dB are achievable. Thus high resolution measurements that are essentially real-time are possible, with data produced every 10 msec or at even higher rates. Wired measurements reduce the need for processing gain, and can enable the most rapid measurements, while wireless measurements that take advantage of the enhanced processing gain require measurement times that are slightly longer (on the order of msec).

Potential Applications for Deposition Monitors

Small, rugged, solid state acoustic wave thin film monitoring devices have the potential to meet the requirements of a number of research and commercial nanomaterial analysis applications, both in deposition systems and in analysis of films such as evaluation of reaction kinetics, changes in film properties, and thermal decomposition analysis, among others. The devices of embodiments of the invention could be used as a research test instrument for characterization of nanomaterials, including nanocluster metal films and carbon nanotubes. As nanomaterials such as CNTs realize widespread commercial application, these devices could be broadly utilized for process control and quality monitoring in nanomaterial manufacturing processes. Monitoring of nanomaterials during deposition processes is one possibility, and verifying product quality or homogeneity during manufacture in a batch testing mode is another. The high temperatures of operation made possible with the proposed materials, combined with the ability to include inherent temperature compensation would allow these devices to be used in a number of applications with harsh environments, such as thermal decomposition analysis of CNTs and other films. Mansfield, E. et. al., "Quartz Crystal Microbalances for Microscale Thermogravimetric Analysis", *Anal. Chem.* 2010, 82, 9977-9982; Mansfield, E. et. al., "Applications of TGA in quality control of SWCNTs", *Anal Bioanal Chem* (2010) 396:1071-1077. Thermogravimetric analysis (TGA) is a widely used analytical method that evaluates the change in sample mass with temperature, providing information on reaction kinetics and changes in material properties with heating. Structural decomposition, changes in film properties (glassy to rubbery, etc), vapor absorption or outgassing, and chemical reactions can all be monitored. Historically TGA has been performed using macroscopic heating and mass measurement techniques, which require the testing of samples of 1 mg or more, an approach that is not well suited to analysis of thin films, nanomaterials, and surface interactions. Mansfield, E. et. al., "Quartz Crystal Microbalances for Microscale Thermogravimetric Analysis", *Anal. Chem.* 2010, 82, 9977-9982; Mansfield, E. et. al., "Applications of TGA in quality control of SWCNTs", *Anal Bioanal Chem* (2010) 396:1071-1077. Monitoring the kinetics of chemical or biological reactions occurring at the surface of the device, or changes in state of an applied film (from glassy to rubbery, as just one example) can also be achieved as discussed previously.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 1(c) shows how this frequency domain response changes with variations in the spacing and relative amplitudes of the two impulse responses. FIG. 1(d) shows two idealized window functions that represent two adjacent half-passband filters used to window the notched frequency response of FIG. 1(c). FIG. 1(d) shows the two frequency responses resulting from the two filters. The relative amplitude and frequencies of these responses vary based on the location of the null(s).

DETAILED DESCRIPTION

Figure 1:
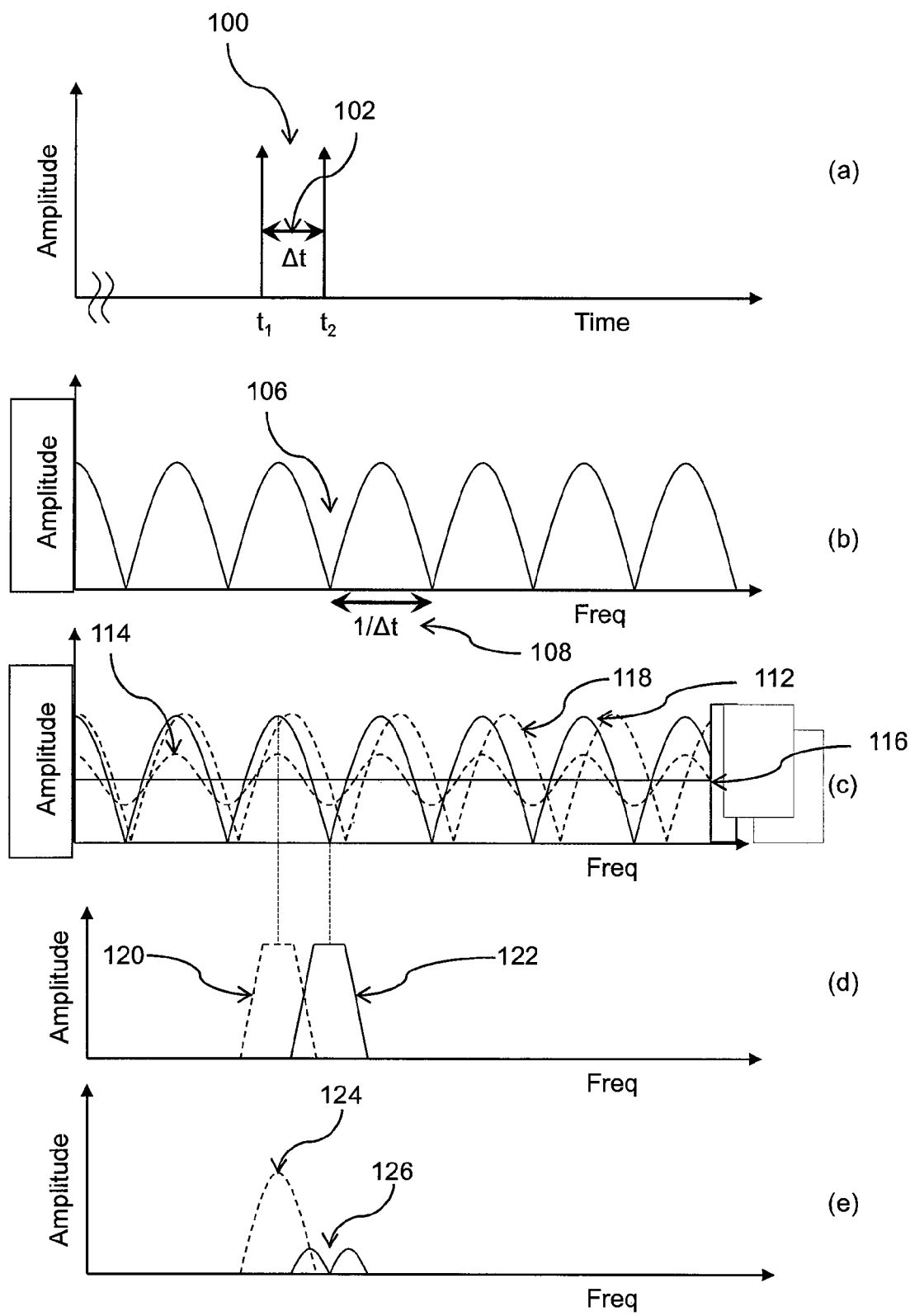
FIG. 1 shows two idealized impulse responses in the time domain (FIG. 1(a)), along with the frequency domain response (FIG. 1(b)) corresponding to this time domain response.

It has been established (see ASR&D U.S. Pat. No. 7,434, 989 SAW temperature sensor and system, issued in 2008, herein incorporated by reference in its entirety) that SAW devices with three acoustic wave elements including at least one transducer can be constructed to produce two responses that are closely spaced in time, resulting in a train of notches in the frequency domain separated by the inverse of the delay difference in responses, windowed by the bandpass function produced by the SAW transducer and reflector elements. FIG. 1 below illustrates idealized versions of the responses described. FIG. 1(a) shows two idealized impulse responses 100 in the time domain, separated by a time spacing $\Delta t$ (102). FIG. 1(b) shows the (positive) frequency spectrum corresponding to the Fourier transform of the signal in FIG. 1(a), which consists of a train of nulls 106 separated in frequency by spacing 1/Δt (108). FIG. 1(c) shows how this train of nulls would change as the amplitude of the two impulses varies, and as the time separation of the two impulses 102 varies. When both impulses are of equal amplitude, as shown in FIG. 1(a), with time spacing Δt (102), the frequency response is a train of deep nulls 112. As the amplitudes of the two impulses become unequal, the nulls become shallower and less distinct 114, until when one of the impulses disappears the response becomes constant 116. If the two impulses have equal amplitudes, but the spacing Δt (102) increases, the nulls in frequency become spaced further apart 118. In a practical implementation of these responses in a SAW device, windowing is produced by the SAW transducers. FIG. 1(d) shows idealized window functions 120 and 122, where the two window functions together create a bandpass filter. As shown in FIG. 1(d), window function 120 is centered on a peak of the frequency response, while window function 122 is centered on the adjacent null of the frequency response. FIG. 1(e) shows an idealized version of the response that would be produced by implementing such a structure in a SAW device. Given the frequency alignment of the two window functions, 120 produces a peak 124, while 122 produces a low response 126. The relative amplitude of the responses in the two half passbands (which together make up one overall passband) provides information about the positions and depths of the nulls in the frequency response.

Proper selection of the device passband (made up of half passbands 120 and 122) and time separation Δt (102) produces a device with one or more nulls in the passband. As the time separation between impulses varies, the string of nulls "accordians" in and out, with the DC end pinned. The sensitivity of the device can be varied by selecting the appropriate separation Δt (102), and by selecting at which null to operate. Nulls farther away from DC move faster for a given change in separation Δt. In addition, for a fixed passband, as the separation Δt (102) varies, the number of nulls in the passband can change. Also, as the relative amplitudes of the two impulses change, the depth and sharpness of the nulls changes.

It should be noted that this technique, including the use of time integrating correlator based measurements, can be extended to utilize multiple passbands rather than simply two window functions, as shown in FIG. 1(d), to provide more detailed information about notch location and movement. Alternatively a single passband window function can be utilized that spans the entire frequency band of interest, with a larger differential delay providing measurement of the relative amplitudes and delays of the two responses, although this embodiment will not provide the enhanced sensitivity of the notched configuration disclosed herein.

Figure 2:
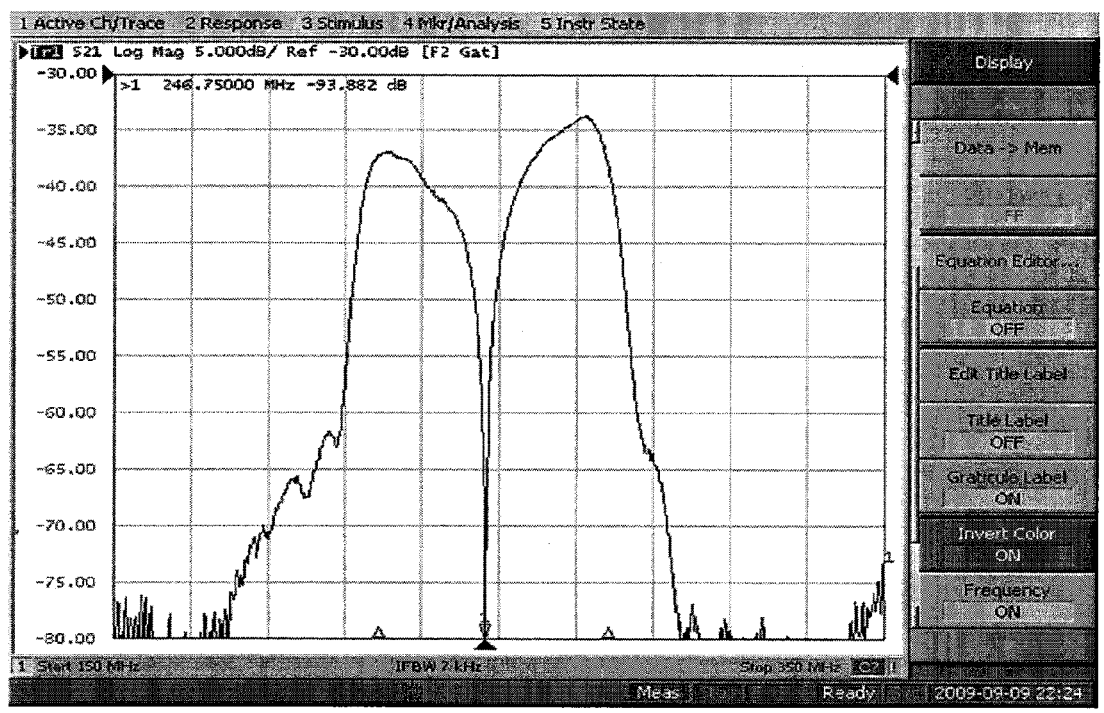
FIG. 2 is an example of the measured frequency response of a SAW differential delay line film deposition monitor device according to an embodiment of the present invention, with a single notch (more than 45 dB in depth) in the passband.

In practice, the actual notches produced can be significantly sharper and narrower in frequency than shown in FIG. 1. FIG. 2 shows a measured response for a simple SAW device according to this structure. In this particular device, the notch is quite narrow, and more than 45 dB in depth. Single null devices are often desired, although devices can be designed to have various numbers of nulls in the passband by proper selection of the windowing functions, and null depths and locations. On prior embodiments, the delay differences that determine the notch frequency and separation have been designed into the devices based on the distances between transduction and/or reflection elements. For useful devices, this generally means the two delays are different by a small delay, resulting in a single notch in the SAW passband frequency range. No films have been utilized in these devices in the past.

Figure 3:
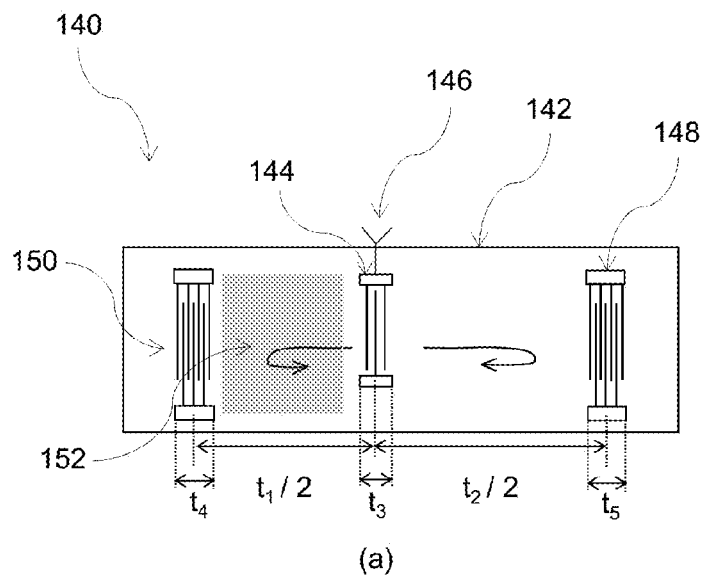
FIG. 3 shows a schematic representation of two embodiments of temperature compensated film deposition and analysis devices. These devices can also be used independently as temperature sensors (with or without the added surface films).
Figure 3:
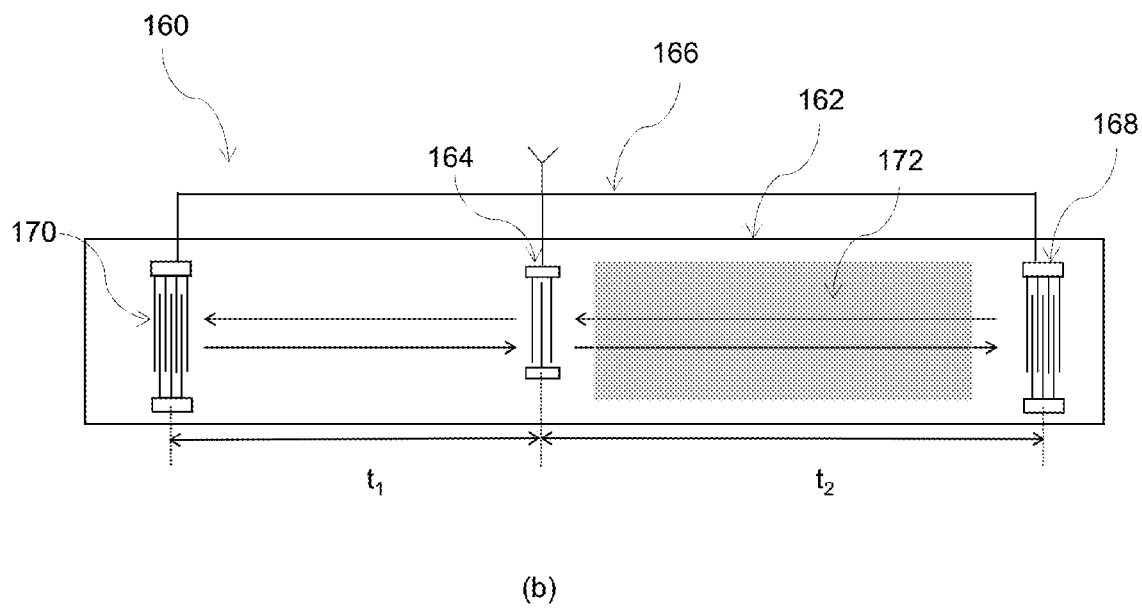

Embodiments of the current invention utilize SAW differential delay line devices with equal to significantly differing delays, that when combined with the films being deposited provide measurable changes in device response based on film deposition and properties. FIG. 3 below shows one such simple device configuration 140. In this embodiment, the sensor can operate in two ways. In the first operational mode (shown in FIG. 3(a)), the device consists of a piezoelectric substrate (also called a die) 142, on which are formed at least three SAW elements, at least one of which is a transducer. In FIG. 3(a), the center SAW element 144 is a transducer, which serves to receive an exciting signal from an input/output antenna 146. Alternatively, these devices can operated in a wired configuration without an antenna. Transducer 144 converts the input electrical signal into a surface acoustic wave signal, that propagates outward in both directions on the surface of the die. Reflections of the acoustic wave from the two outer SAW elements 148 and 150 (which are shown in this example as transducers, but can be reflectors or transducers) are combined at the center transducer 144, producing an output signal that is transmitted through antenna 146 or alternatively through a direct electrical connection such as a coaxial cable. The reflection from the left SAW element 150 reaches the output port of device 140 at a delay $t_1$, while the reflection form the right SAW element 148 reaches the output port of device 140 at a delay $t_2$. Times $t_1$ and $t_2$ are selected to produce the desired starting separation Δt. The time duration of the impulse response signal reflected from the left SAW element 150 is $TD_1=(t_3+t_4+t_3)$ and the time duration of the impulse response signal reflected from the right SAW element 148 is $TD_2=(t_3+t_5+t_3)$, where $t_3$ is the time duration of the signal produced in response to application of an impulse by transducer 144, $t_4$ is the time duration of the signal produced in response to application of an impulse by transducer (or reflector) 150, and $t_5$ is the time duration of the signal produced in response to application of an impulse by transducer (or reflector) 148. This is due to the fact that in this reflective device embodiment, the output impulse response signal produced by the left side of the device is the convolution of the impulse impulse of transducer 144. SAW element 150 and transducer 144, while the output impulse response signal produced by the right side of the device is the convolution of the impulse response of transducer 144, SAW element 148, and transducer 144. The delays $t_1$ and $t_2$ and the signal impulse response time durations $TD_1$ and $TD_2$ are designed to ensure that the two impulse response signals (from the left and from the right side of the device) overlap in time. This overlap introduces destructive interference between the two signals, producing one or more notches in the frequency domain representation of the impulse response of the device. The number of notches and location of the notches in frequency will be determined by the difference between delays $t_1$ and $t_2$ and these notches occur for device excitation of any length, i.e. in the time domain, the response signals from the left and the right of the device overlap in time no matter how short the excitation pulse.

In the second operating mode (shown in FIG. 3(b)), device 160 consists of a piezoelectric substrate (or die) 162, on which are formed at least three SAW elements, at least one of which is a transducer. In FIG. 3(b), the center SAW element 164 is a transducer, as are the two outer SAW elements 168 and 170. All three transducers (164, 168, and 170) are electrically connected to a means to provide electrical excitation and to receive the device response, shown in this example by an input/output antenna 166, which is electrically connected to all three said transducers in parallel. Alternatively, these devices can operated in a wired configuration without an antenna. Transducer 164 converts the input electrical signal into a surface acoustic wave signal, that propagates outward in both directions on the surface of the die. At the same time, transducers 168 and 170 excite acoustic waves (either bidirectionally or preferentially in a unidirectional manner towards transducer 164). As the SAW device response is reciprocal, the signal from the acoustic wave launched by 164 and received by 168 is equal to that launched by 168 and received by 164. Likewise, the signal from the acoustic wave launched by 164 and received by 170 is equal to that launched by 170 and received by 164. All four of these signals are combined at the common output means 166, producing an output signal that is transmitted through antenna 166 or alternatively through a direct electrical connection such as a coaxial cable. The portion of the response from SAW elements 164 and 170 reaches the output port of device 160 at a delay $t_1$, while the portion of the response from SAW elements 164 and 168 reaches the output port of device 140 at a delay $t_2$. As before, times $t_1$ and $t_2$ are selected to produce the desired starting separation $\Delta t$. Also as before, time durations of the impulse responses from the left of the device and from the right of the device and delays $t_1$ and $t_2$ are designed to ensure that the two impulse response signals (from the left and from the right side of the device) overlap in time.

In each of these implementations, the nominal delay on each side of the device, indicated by $t_1$ and $t_2$ in FIG. 3, and the time durations of the impulse response of the signals generated by the left and right side of the device $TD_1$ and $TD_2$ respectively, are selected to provide overlapping time domain responses with the desired differential delay, producing the desired notch(es) in the passband before changes in temperature or deposition of the film to be measured. It should be noted that the two-sided layout of the devices in FIG. 3 could equally well be implemented using a multi-track one-sided die, with both reflectors or output transducers on one side of the input/output transducer. In such a configuration, a single phase unidirectional transducer (SPUDT) could be beneficial for each transducer. It should also be noted throughout that the SAW elements described could be implemented using conventional, slanted, tapered, or stepped-tapered electrode structures.

Devices such as those shown in FIG. 3 can be used as temperature sensors, to provide temperature compensation for the measured film properties. In this application, the delays $t_1$ and $t_2$ each change as temperature varies, in a manner determined by the properties of the piezoelectric substrate. For instance, for YZ-lithium niobate, when temperature increases from room temperature, the substrate softens, causing the acoustic velocity to be slower, and the delay times $t_1$ and $t_2$ to both increase. The temperature coefficient of delay for this material is |TCD|=93 ppm/° C. However, the increase is proportional to the initial delays, and so the longer delay increases by slightly more than the shorter delay. Consider, by way of example, a delay $t_1$ that is initially 1 μsec long and delay $t_2$ that is initially 1.01 μsec long. For this starting separation $\Delta t$=10 nsec, producing a null-to-null separation of 100 MHz. The third null, for this example, would be at 250 MHz. For a change in temperature of −10° C., delay $t_1$ would shrink to 0.99907 μsec long and delay $t_2$ that is initially 1.01 μsec long would shrink to 1.0090607 μsec long. The separation is now $\Delta t$=9.9907 nsec, producing a null-to-null separation of 100.093 MHz, 93 kHz larger than the starting value. This places the third null at 250.233 MHz, fully 233 kHz higher in frequency than the starting point. Thus, this sensor can detect temperature with a sensitivity of 23.3 kHz/° C. If a higher number null is considered—say the sixth null—which initially is at 550 MHz, the modified null location when the temperature drops 10° C. will be 550.5115 MHZ, a 511.5 kHz shift in 10° C., or 51.15 kHz/° C. Thus, evaluating nulls farther out from the origin in FIG. 1(b) produces a temperature sensor with higher sensitivity. Almost arbitrary temperature sensitivity is achievable through proper device design, removing the prior limitation due to dependence on solely the substrate properties. Additional methods to achieve higher sensitivity, such as using propagation on two different directions with slightly differing TCDs, or adding a surface film to deliberately introduce a difference in TCDs between the two acoustic propagation paths without using different acoustic propagation directions are also possible.

To provide a temperature compensated deposition monitor device, devices according to FIG. 3, with parallel or non-parallel acoustic propagation paths can be used as discrete devices, mounted on a common header that is thermally in contact with the deposition monitor device. Alternatively, this structure can be incorporated directly onto the die of the deposition monitor device. This temperature compensation device can be chosen to operate in the same frequency band as the deposition monitor device, or in a frequency band that is distinct from that of the deposition monitor device. Whether on the same die as the deposition monitor or on a physically discrete die, the temperature sensor portion of the apparatus (or device) will be shielded from the film being deposited, in order that it is affected only be changes in temperature. Physical shielding can be used to prevent co-deposition of the temperature sensor region, while leaving the device open to variations in other system parameters such as pressure. Alternatively, the temperature sensor device can be hermetically sealed to ensure only temperature affects device response. An alternate method for temperature compensation is described below.

Figure 6:
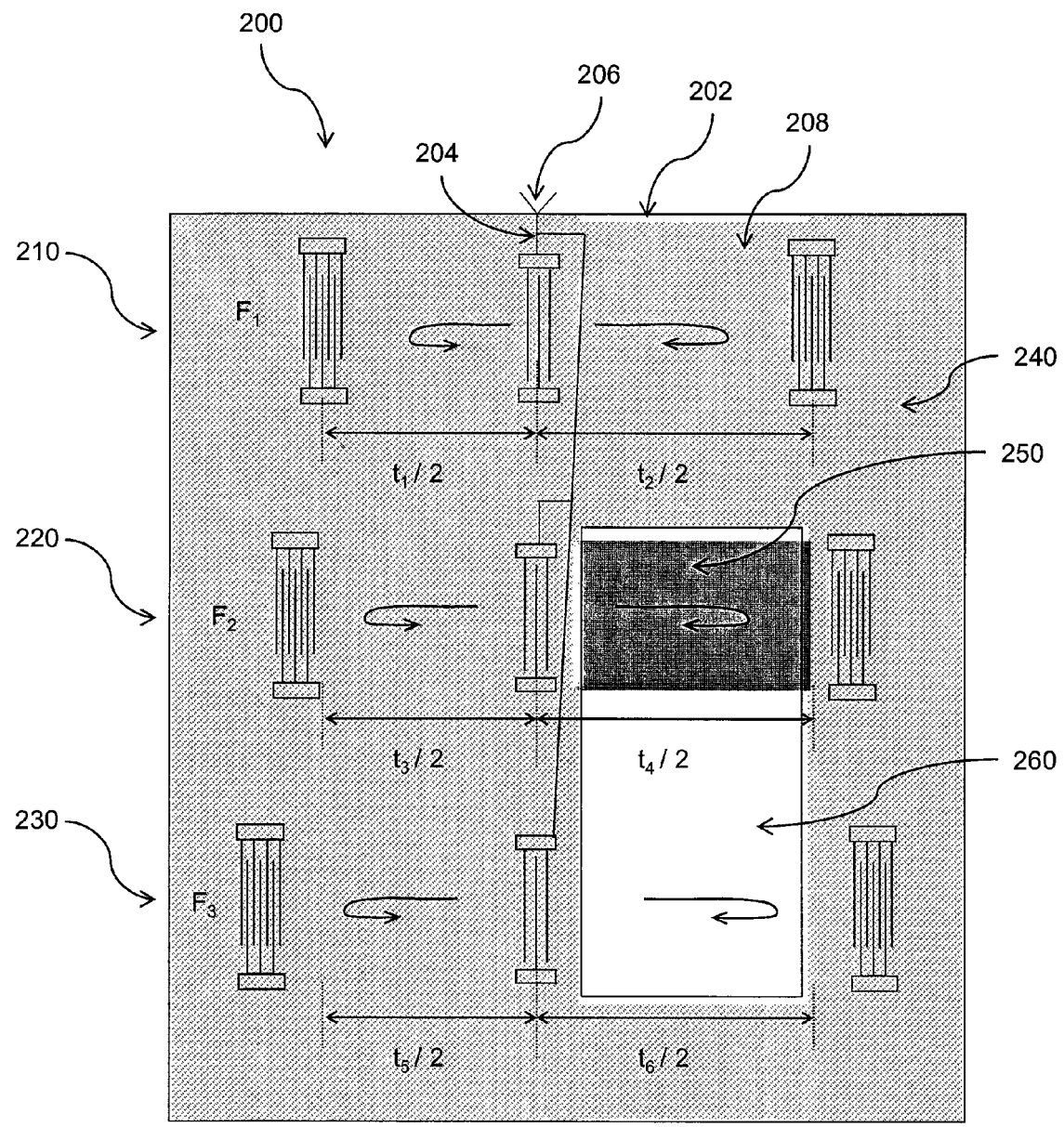
FIG. 6 shows a schematic representation of a composite SAW deposition monitor device according to an embodiment of the present invention. Included are a temperature sensor reference acoustic channel (top), an acoustic channel for obtaining mass loading and viscoelastic effects (center), and a channel from which electrical interactions can be obtained (bottom). With all three tracks present, it is possible to extract all of the desired information regarding the film or surface reaction of interest. Also shown is a masking means that confines deposition of the film to the desired regions of the device.
Figure 7:
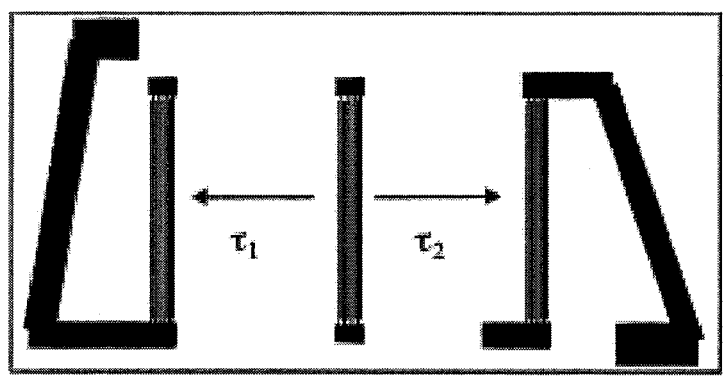
FIG. 7 shows a schematic representation of a simple reflective differential delay line (RDDL) filter. The differential delay is selected to produce the desired number and location of notches in the frequency domain passband. Film deposition can be performed onto the region between the left and center transducer, or the center to the right transducer, depending on desired performance.
Figure 8:
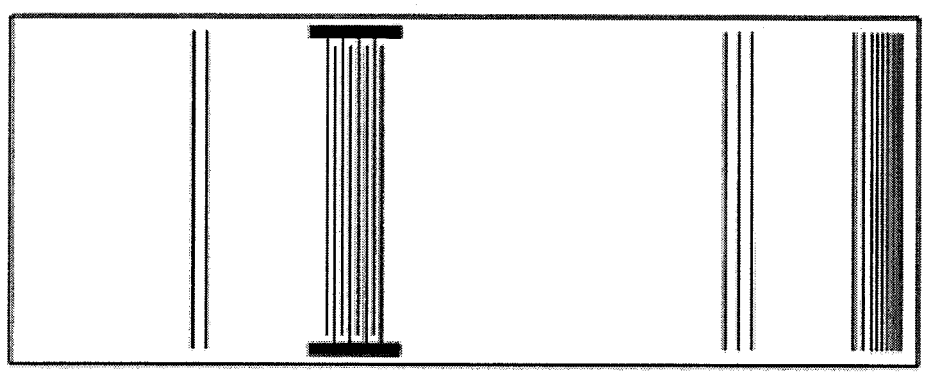
FIG. 8 shows a schematic representation of a coded reflective differential delay line filter. In this example of a coded filter device structure, coding similar to orthogonal frequency coding (OFC) is implemented in the reflector structures. Again, the differential delay is selected to produce the desired number and location of notches in the frequency domain passband, and film deposition can be performed onto the region between the left reflector and the center transducer, or between the center transducer and the right reflector, depending on desired performance.
Figure 9:
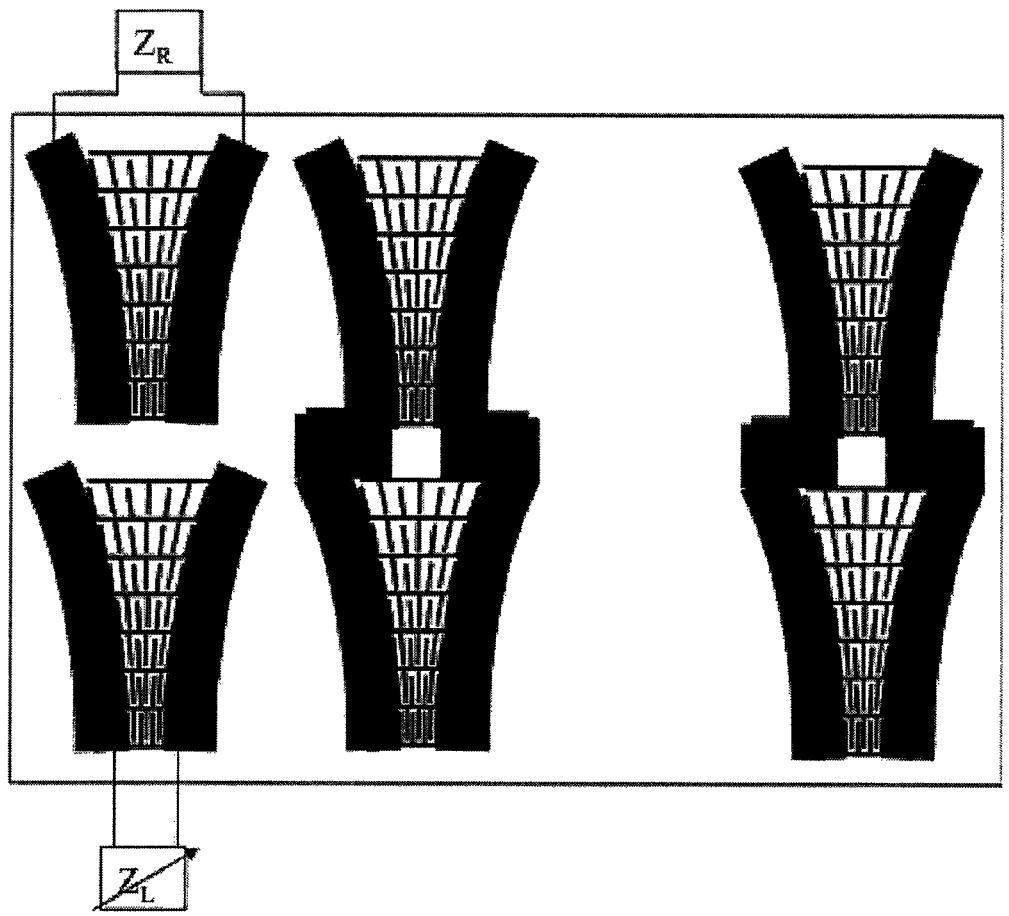
FIG. 9 shows a schematic representation of a tapered, two acoustic track differential delay line filter, incorporating reference and variable loads on two ports.
Figure 10:
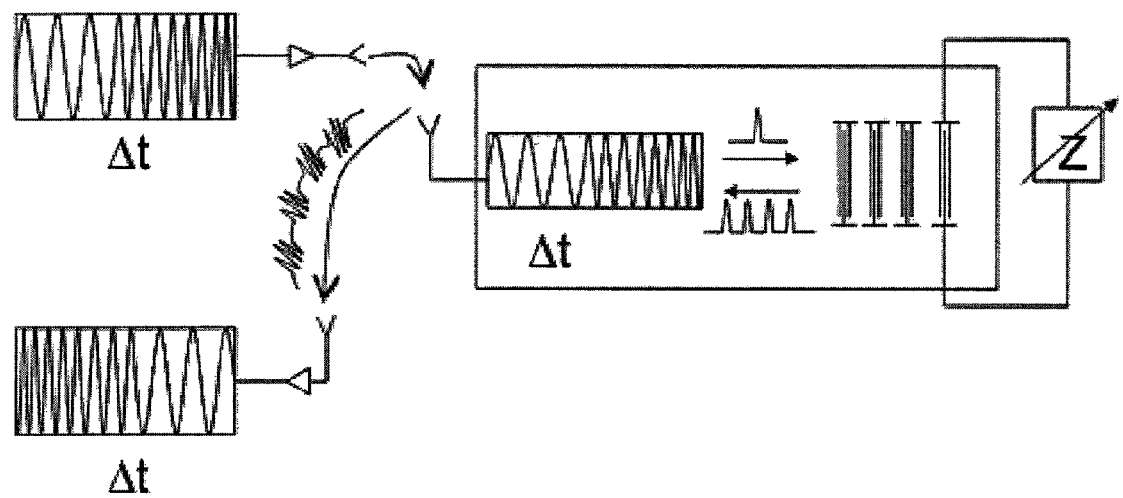
FIG. 10 shows a schematic representation of a fully dispersive reflective RFID device with external load varying based on deposited film. Another embodiment can also be implemented with a multi-track or two-sided (dispersive of non-dispersive) RFID device with the film deposited in selected regions that impact one or more of the reflected responses.
Figure 11:
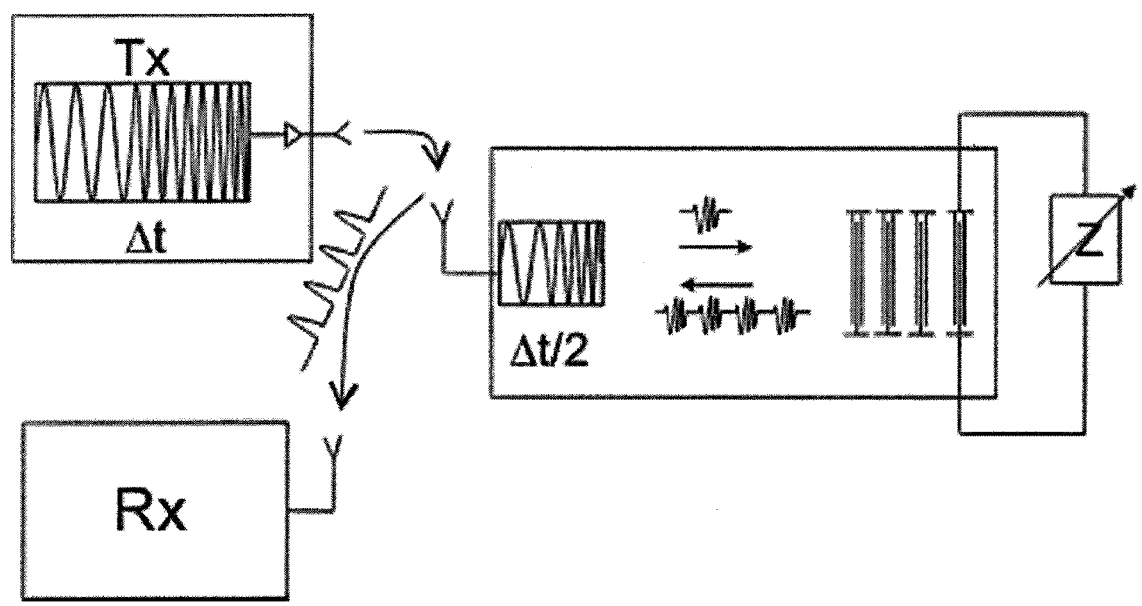
FIG. 11 shows a schematic representation of a half-dispersive reflective RFID device with external load varying based on deposited film. Another embodiment can also be implemented with a multi-track or two-sided (dispersive of non-dispersive) RFID device with the film deposited in selected regions that impact one or more of the reflected responses.

Film deposition is monitored by constraining deposition of the film to occur on a defined region of the deposition monitor device, said region located between the input/output transducer 144 of FIG. 3(a) and either SAW element 148 or 150. In FIG. 3(a), this is represented graphically by the region 152, while in FIG. 3(b) it is represented by region 172. This can be accomplished by physical or other masking. The region of the film deposition is the sensing path, while the acoustic path on which no film is deposited is the reference path. The deposition of the film to be measured modifies the delay on the sensing path, changing the spacing $\Delta t$ and thereby changing the null locations (and potentially the number of nulls in the passband), and simultaneously can change the relative amplitudes of the two responses, changing the depth and sharpness of the nulls. These changes in notch structure are produced in real-time during film deposition and can be monitored using a network analyzer or other appropriate system. The longer the acoustic propagation path under the film, the greater the changes observed in device performance will be for given film properties. In the devices of FIG. 3, the die length of die 162 has been increased relative to that of die 142, with the intent that the overall delay of the reflected paths in FIG. 3(a) would be equal to the single-transit acoustic path delays of FIG. 3(b). Since the acoustic wave in FIG. 3(a) transits the film region twice, the overall effect of a film of length "L" on the device of FIG. 3(a) would be equivalent to the effect of a film with the same properties but of length "2*L" on the device of FIG. 3(b). As another option for temperature determination, the reference peak in time provides a built-in reference. Changes in device temperature will produce shifts in the delay of this reference device. This can be used to calibrate the devices for film thickness at varying deposition temperatures. The changes in the second peak relative to the reference peak can be used to determine the film response (as distinct from the effects of temperature). This configuration is best used in a wired configuration, where the nominal delay and amplitude of the reference peak at a known temperature can be established for calibration purposes. For wireless applications, were the RF propagation delay to the sensor may be unknown, a device utilizing differential delay lines for each parameter measured, such as that shown in FIG. 6, is preferred.

As shown in FIG. 3, the film can be deposited on the nominally shorter or the nominally longer acoustic path, depending on the anticipated film properties and how these should change device performance. If properties are unknown, multiple devices (standalone or combined) can be used to evaluate deposition on the short and long paths separately. It should be noted that the nominal separation Δt prior to film deposition can be zero. In this case, $t_1$ and $t_2$ are equal prior to film deposition, and no nulls occur in the passband. This provides a deposition device that is inherently temperature compensated for use with ultra-thin films. It is inherently temperature compensated because the changes in acoustic propagation due to changes in temperature will be the same for both acoustic propagation paths, which are equal. Thus, any temperature induced changes will cancel out, leaving the separation Δt at zero. Only changes due to deposited films will be sensed. These film-induced changes will modify the device response, introducing nulls that may become visible in and move through the passband. Provided the film is not thick enough to experience temperature dependent film properties, this device will retain its temperature compensation. Of course, this is only the case for extremely thin films, and primarily for films where conductivity plays a more significant role than viscoelastic properties or mass loading.

Figure 4:
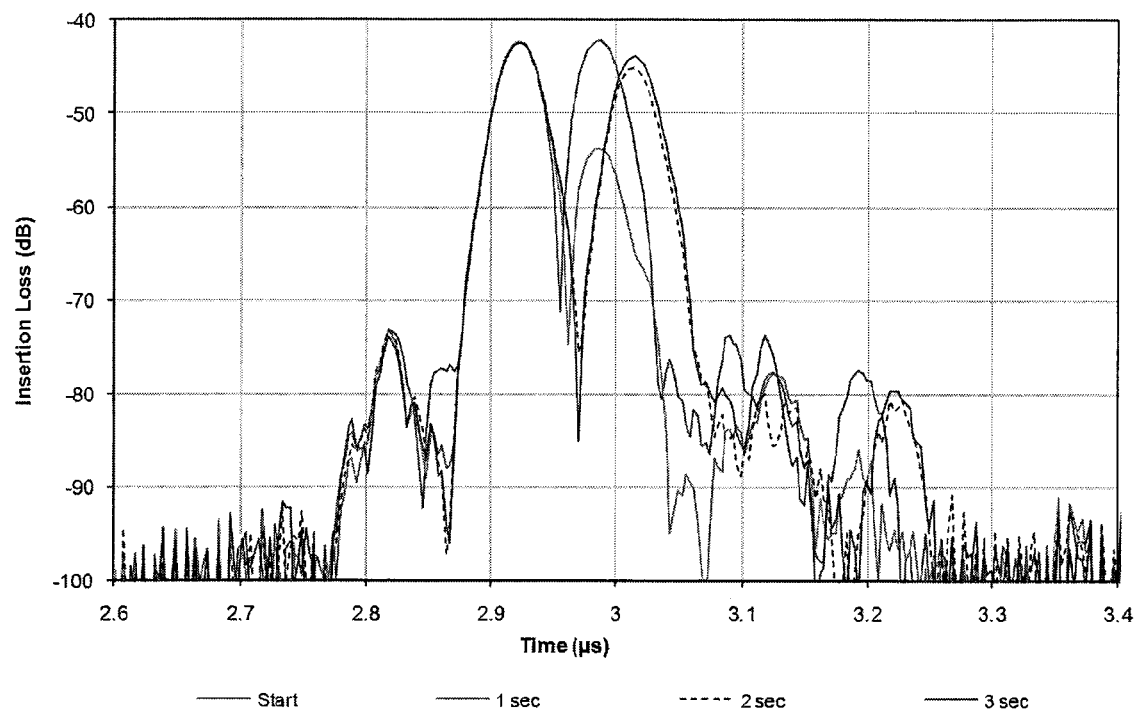
FIG. 4 shows the experimental time lapse response of an in-situ SAW deposition monitor according to an embodiment of the present invention during e-beam deposition of an ultrathin Palladium (Pd) film. The film measured 14 angstroms on the QCM monitor, and was deposited over only 4 seconds. Note that this response (in the time domain) has a reference signal (the peak on the left, which remains unchanged during the deposition), and a measurement peak that changes during exposure (on the right).
Figure 5:
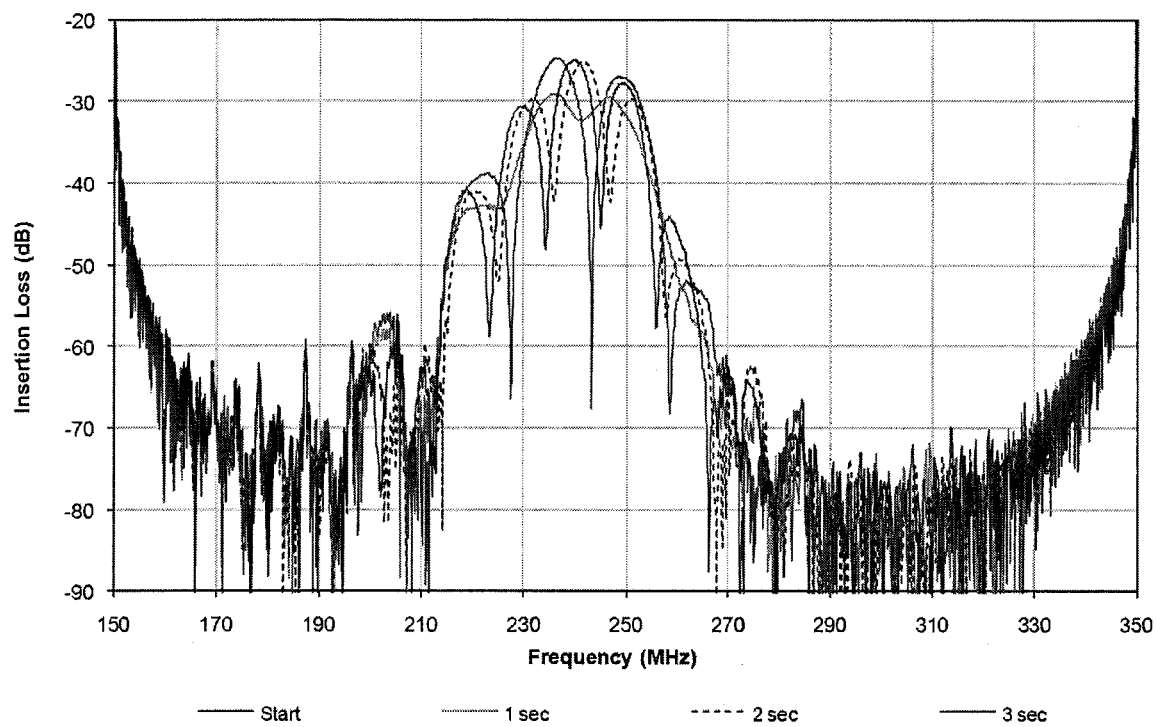
FIG. 5 shows the frequency domain responses corresponding to the time domain responses shown in FIG. 4.

During NASA SBIR contract NNX10CD41P, "Rapid Hydrogen and Methane Sensors for Wireless Leak Detection" (Hines, J. H., NASA Contract Number NNX10CD41P, "Rapid Hydrogen and Methane Sensors for Wireless Leak Detection", Phase I SBIR Final Report, 29 Jul. 2010), lack of reproducibility of the ultrathin nanostructured Pd films being deposited in this project and in prior ASR&D hydrogen sensor research was identified as a key factor that needed to be addressed in order to make commercial production of these sensors feasible. The standard QCM deposition monitors used to track film thickness during deposition were shown to be insufficient for the ultrathin films in question. To meet this need, a real-time in-situ monitor was developed and used to monitor ultra-thin film Pd deposition by e-beam evaporation. As shown in FIGS. 4 and 5 below, these ultra-sensitive devices can monitor second by second film formation. The experimentally observed changes in device response are quite large, even for the Pd film shown in this example, which measured only 14 angstroms in thickness on the QCM deposition monitor (although subsequent measurements showed this thickness was not accurate).

FIG. 4 shows the measured time domain response of a simple SAW deposition monitor according to an embodiment of the present invention. The starting condition of the device response is shown by the red curve on FIG. 4, and consists of two peaks in time, which correspond to the reflections from the two reflective structures at either end of the SAW device (similar to that shown in FIG. 3(a)). As the film thickness increased, the second peak in the time domain response shown in FIG. 1 changed from −44 dB down to −55 dB after one second, down to more than −100 dB (in the noise) after 2 seconds, and then came back up to −45 dB after 3 seconds. For this particular run, this happened in a period of less than 4 seconds. Other deposition runs performed at lower deposition rates showed more gradual changes. Note in FIG. 4 that the reference peak in time provides a built-in reference. Changes in device temperature would produce shifts in the delay of this reference response. This can be used to calibrate the devices for film thickness at varying deposition temperatures. The changes in the second peak relative to the reference peak can be used to determine the film response. For the responses shown in FIG. 4, it is clear that there is essentially no change in temperature, as evidenced by the lack of change in the delay of the reference peak. The sensing peak, by comparison, changes in both amplitude and delay, with amplitude initially increasing and then decreasing, and delay increasing as film thickness increases. Note that the shift to higher delay for the sensor response can be seen most clearly, perhaps, at low film thickness by considering the location in time at which the two responses overlap, which appears as a relative minima in the combined signal (as the response peak may not retain symmetry as the two responses change in amplitude relative to one another, and thus peak location can be problematic).

FIG. 5 shows the frequency domain response measured for the device whose time domain response is shown in FIG. 4. The device in the initial state, prior to film deposition, has three sharp nulls in the passband region. As in the time domain response, drastic changes in the frequency domain response are observed with minute incremental film deposition steps. After 1 second of deposition, the nulls have all become very shallow and poorly defined, as the device is in transition between having three and four nulls. This corresponds to the sensor response amplitude decreasing to substantially less than the reference peak amplitude (green curve in FIG. 4). After 2 seconds, the device has four sharp nulls in the passband. And after 3 seconds, a fifth null is entering the passband region from the high frequency side.

The size of the changes observed in the frequency response notches, both in depth (amplitude) and in frequency, are quite large. Notches vary by over 40 dB in depth, and by many MHz in frequency in the simple example shown in FIG. 5. The time resolution of the measurement system used for data collection in this preliminary experiment limited sample rate to 1 sample per second. Alternate wired and wireless interrogation systems are possible that can provide significantly faster data acquisition, easily up to one sample every 10 msec, and potentially higher rates depending on other system performance factors required.

Atomic force microscope (AFM) scratch tests measurements performed subsequent to this experiment were used to calibrate the deposition monitor response, and showed that the films in this example were actually 34 Å, not the 14 Å reported by the QCM device. The large changes observed for this film were determined to be primarily due to changes in film conductivity as film thickness increased, with a small contribution due to mass loading.

As shown above, embodiments of the present invention provide a highly sensitive measurement tool for extremely thin films. These devices can be customized for measurement of conductive, non-conductive, and semi-conductive films. Deposition of continuous and non-continuous films can be monitored. Discontinuous films such as nanoclustered metal films, that can exhibit non-conventional conductivity mechanisms such as quantum mechanical electron tunneling, can be monitored using these devices based on the changes in conductivity during deposition. This is particularly significant since the mass loading and elastic properties of such thin, discontinuous films can be minor at very small film thicknesses, and can be much smaller than the changes in electrical film properties.

In order to extract information about the film being deposited, it is worthwhile to measure conductive effects as well as effects of mass loading and viscoelasticity, and to separate these effects from one another to the extent possible. Inclusion of a temperature sensor device allows extraction of the effects of temperature, which can be done using the delay of the integral reference peak(s), or with separate temperature sensing elements as discussed above. Inclusion of multiple differential delay lines, preferably operable in different frequency ranges, with different coating treatments allows separation of conductive effects from those involving mass loading and viscoelasticity. FIG. 6 shows a preferred embodiment of a composite deposition monitor device 200 incorporating these features. Deposition monitor device 200 consists of piezoelectric substrate 202, on which a minimum of three SAW elements have been formed. The embodiment of FIG. 6 includes three acoustic channels 210, 220, and 230, which have SAW elements designed to operate in passbands centered at frequencies $F_1$, $F_2$, and $F_3$. These can be chosen coincident, but separating the three operating frequencies to produce three separate passbands is advantageous in that it allows production of one or more nulls as desired in each passband. These three channels can be spatially separated, or can be subchannels defined transversely across the aperture of a one or more transducers. The three input/output transducers can be fed electrically in common, as shown with feed 204, or can be accessed separately. Each channel shows outer SAW elements acting as reflectors, but once again either reflectors or transducers, or a mixture of both can be used. Device 200 includes a metal film 250 in one acoustic path of one channel. This metal pad shorts out the electric field at the surface of the device, meaning that any film deposited on this region will modify the SAW propagation only due to mass loading and viscoelastic film properties. Electrical properties of the film will not affect the SAW in this region. Shown in FIG. 6 is a mask 240, that is designed to cover the entire device 200 with the exception of region 260, which is an open window through which film deposition is performed. As shown in the embodiment of FIG. 6, the mask 240 leaves a rectangular window 260 open, to allow deposition of the film on the acoustic propagation paths of one side of acoustic channel 220, which has a metal shorting pad on it, and one side of acoustic channel 230, which is bare substrate. The third acoustic channel, 210, is used to measure temperature. This structure allows the effects of electrical film properties to be determined from the response of channel 230, with the response of mass loading and viscoelastic properties from channel 220 subtracted, and the temperature response from channel 210 taken into consideration. The times $t_1, t_2, t_3, t_4, t_5$, and $t_6$, and impulse response signal durations of each component signal can be selected to produce the desired passband and notch configurations in each acoustic channel.

One skilled in the art will recognize that there are a wide range of device embodiments that can be used to implement deposition monitor devices according to embodiments of the present invention. A selection of these device types (in addition to those described previously) is shown below. All of these devices can be implemented in single-track formats, or in multiple acoustic track formats. They can be provided with electrical shorting pads in the deposition region(s) or portions thereof and/or the reference acoustic path(s) or portions thereof, if beneficial for the desired application (to separate the electrical effects of the deposited film from the mass loading and viscoelastic properties).

The transducers and/or reflectors described thus far are all non-dispersive, and similar embodiments could be envisioned that utilize transducers that are tapered, slanted, stepped tapered, apodized, withdrawal weighted, EWC, UDT, SPUDT, dispersive, and/or waveguide structures. Even a reflective array compressor structure could be used to implement such a deposition monitor, although such a device structure would be unnecessarily complex for most applications. All of these techniques could also be used incorporating dispersive and harmonic techniques.

Also, one skilled in the art will recognize that these devices can be implemented on various substrate materials, and can utilize various acoustic wave propagation modes, in order to achieve performance required for specific applications. Performance to measure deposition of vapors, liquids, polymers, solids, and numerous other quantities can be achieved. Measurement of films deposited at high temperatures can be accomplished using langasite, langanite, of langatate, or other substrate capable of operating at high temperatures. In order to measure conductive films, a substrate with high electromechanical coupling coefficient is preferred. Electrodes and busbars of SAW elements can be made from materials appropriate to survive the application environment, including the ability to withstand high or low temperatures, and chemical environments. Generally, the masking during film deposition will preferentially be done in a manner to prevent the exposure of any of the electrode structures to the film being deposited.

Any of a wide range of known coding and other diversity techniques can be implemented in the transducers and/or reflectors. It would be understood by one versed in the art that simple on-off keying, phase modulation, pulse position modulation, and many other techniques could be used to enhance the number of codes available. The use of multiple delay "slots" within each code reflector nominal delay position is widely used to achieve increased code set size, and the use of multiple pulses per data group is also well known. Frequency diversity, code diversity, time diversity, and other know techniques can be combined to achieve sets of devices with desirable properties. Any of these techniques could be utilized in the aforementioned device embodiments to increase the number of sensors that can work together in a system with individually identifiable devices. Devices utilizing such structures could be useful for RFID tag applications, where more than one deposition monitor is required within a system, and identification of individual devices is desired.

The broad nature of the embodiments described here are clear, and one skilled in the art will understand that there is a wide variety of device configurations that can be generated using combinations of one or more of the techniques discussed. The inventions described herein and illustrated in the figures provide device embodiments capable of monitoring deposition of a wide range of materials, including but not limited to ultrathin films and nanomaterials. Embodiments of the present invention can be interrogated using, among other techniques, a preferred time integrating correlator system such as that disclosed in U.S. Pat. No. 7,434,989, herein incorporated by reference in its entirety. While the preferred forms and embodiments of the invention have been illustrated and described, it will be apparent to those of ordinary skill in the art that various changes and modification may be made without deviating from the inventive concepts set forth above.

The present invention has been described in relation to particular examples, which are intended in all respects to be illustrative rather than restrictive. Those skilled in the art will appreciate that many different combinations of materials and components will be suitable for practicing the present invention.

Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A surface acoustic wave film deposition monitoring and analysis device, comprising
   (a) a piezoelectric substrate;
   (b) at least one first transducer arranged on at least a portion of said piezoelectric substrate wherein said first transducer has electrode structures so as to be capable of generating and receiving acoustic waves at desired frequencies, and wherein said first transducer has an impulse response time duration of td1;
   (c) at least one second surface acoustic wave element formed on said piezoelectric substrate and spaced from said first transducer along the direction of acoustic wave propagation at a distance to create a first acoustic delay, said at least one second surface acoustic wave element comprising electrode structures capable of interacting with acoustic waves at frequencies that correspond to the frequencies generated by said first transducer, and wherein said second SAW element has an impulse response time duration of td2;
   (d) at least one third surface acoustic wave element formed on said piezoelectric substrate and spaced from said first transducer along the direction of acoustic, wave propagation at a distance to create a second acoustic delay, said at least one second surface acoustic wave element comprising electrode structures capable of interacting with acoustic waves at frequencies that correspond to the frequencies generated by said first transducer, and wherein said third SAW element has an impulse response time duration of td3;
   (e) wherein said second and third acoustic wave elements interact with the acoustic wave launched by said first transducer to produce first and second signals occurring at first and second acoustic delays, $t_1$ and $t_2$, respectively;
   (f) wherein the time duration TD1 of the first signal produced through application of an impulse to said first transducer, and as a result of the acoustic wave generated by said impulse interacting with said first transducer and said second SAW element, is equal to at least the sum of the time duration of the impulse response of said first transducer (td1) plus the time duration of the impulse response of said second SAW element (td2) (TD1≥td1+td2);
   (g) wherein the time duration TD2 of the second signal produced through application of an impulse to said first transducer, and as a result of the acoustic wave generated by said impulse interacting with said first transducer and said third SAW element, is equal to at least the sum of the time duration of the impulse response of said first transducer (td1) plus the time duration of the impulse response of said third SAW element (td3) (TD2≥td1+td3);
   (h) wherein said first and second delays t1 and t2 are unequal, causing a separation $\Delta t=|t_1-t_2|$ between the centers of said first and second signals;
   (i) wherein the durations TD1 and TD2 of said first and second signals are longer than said separation Δt, such that said first and second signals overlap in time; and
   (j) wherein the combined response of said first and second signals effect a composite impulse response signal comprising a bandpass filter response in the frequency domain with one or more notches (also known as nulls) in the passband;
   (k) further comprising a masking means that confines to the desired at least one region of said device the deposition of the film to be monitored.

2. A surface acoustic wave film deposition monitoring and analysis device, comprising:
   (a) A surface acoustic wave film deposition monitoring and analysis device as in claim 1;
   (b) further comprising a surface treatment applied on a portion of one of the acoustic propagation paths that generate said first or second acoustic delay;
   (c) wherein the nominal separation in time of said first and second acoustic responses is equal to zero prior to application of said surface treatment in a confined region of the surface of said device;
   (d) wherein modification of the acoustic wave propagation velocity in the region of the surface treatment modifies the acoustic delay of one of said responses; and
   (e) wherein said modification produces a non-zero separation Δt in time of said first and second signals, effecting one or more notches (nulls) in the frequency domain impulse response of the device.

3. A surface acoustic wave film deposition monitoring and analysis device, comprising:
   (a) A surface acoustic wave film deposition monitoring and analysis device as in claim 1;
   (b) wherein deposition of a film onto a confined region of the device surface, defined by said masking means, that comprises a portion of one of the acoustic propagation paths that generate said first or second acoustic delay, causes a change in said separation Δt in time of said first and second signals, to alter the properties of said one or more notches (nulls) in the frequency domain impulse response of the device.

4. A surface acoustic wave film deposition monitoring and analysis device, comprising:
   (a) A surface acoustic wave film deposition monitoring and analysis device as in claim 1;
   (b) wherein said first and second delays $t_1$ and $t_2$ differ by no more than 100 nanoseconds, causing a separation Δt≤100 nanoseconds between the centers of said first and second signals.

5. A surface acoustic wave film deposition monitoring and analysis device, comprising:
   (a) A surface acoustic wave film deposition monitoring and analysis device as in claim 1;
   (b) wherein said first and second acoustic delays $t_1$ and $t_2$ differ by no more than 20 nanoseconds, causing a separation Δt≤20 nanoseconds between the centers of said first and second signals.

6. A surface acoustic wave film deposition monitoring and analysis device, comprising:
   (a) A surface acoustic wave film deposition monitoring and analysis device as in claim 1;
   (b) further comprising at least two acoustic tracks, each containing at least two SAW elements, at least one of which is a transducer;
   (c) wherein at least one of said acoustic tracks is protected by said masking means to prevent deposition of said film to be monitored onto said protected acoustic track;
   (d) wherein said protected track provides a reference response that is not modified by deposition of said film; and
   (e) wherein the difference in amplitude and delay between the reference response and the sensing response provide measures of changes in the film being deposited or the surface reaction or modification being sensed.

7. A surface acoustic wave film deposition monitoring and analysis device, comprising:
(a) A surface acoustic wave film deposition monitoring and analysis device as in claim 6;
(b) wherein the signal produced by said at least one protected acoustic track provides a measure of temperature.

8. A surface acoustic wave film deposition monitoring and analysis device, comprising:
(a) A surface acoustic wave film deposition monitoring and analysis device as in claim 6;
(b) further comprising at least three SAW elements in at least one of said at least two acoustic tracks;
(c) wherein said at least three SAW elements are arranged to produce at least one differential delay line response.

9. A surface acoustic wave film deposition monitoring and analysis device as in claim 8, wherein said differential delay line has a small enough differential delay that the two acoustic responses comprising the differential delay line response are overlapping in time, producing a differential delay line response signal that has at least one notch in the passband of the frequency domain representation of the impulse response of said device.

10. A surface acoustic wave film deposition monitoring and analysis device as in claim 8, wherein said differential delay line has a large enough differential delay that the two acoustic responses comprising the differential delay line response are non-overlapping in time, producing a differential delay line response signal that does not have any notches in the passband of the frequency domain representation of the impulse response of said device.

11. A surface acoustic wave film deposition monitoring and analysis device, comprising:
(a) A surface acoustic wave film deposition monitoring and analysis device as in claim 1;
(b) further comprising at least three acoustic tracks, each containing at least two SAW elements, at least one of which is a transducer;
(c) wherein at least one of said at least three acoustic tracks is protected by said masking means to prevent deposition of said film to be monitored onto said protected acoustic track;
(d) wherein at least one of said at least three acoustic tracks has a portion of the acoustic wave propagation path exposed by said masking means to allow deposition of said film to be monitored onto said exposed region of said acoustic track; and
(e) wherein at least one of said at least three acoustic tracks has a portion of the acoustic wave propagation path both exposed by said masking means to allow deposition of said film to be monitored onto said exposed region of said acoustic track and coated with a conductive material.

12. A surface acoustic wave film deposition monitoring and analysis device as in claim 11, wherein said protected acoustic track provides a measure of temperature.

13. A surface acoustic wave film deposition monitoring and analysis device, comprising:
(a) A surface acoustic wave film deposition monitoring and analysis device as in claim 11;
(b) further comprising at least three SAW elements in at least two of said at least three acoustic tracks;
(c) wherein said at least three SAW elements are arranged to produce at least two differential delay line responses;
(d) further comprising at least two different pedestal acoustic delays;
(e) wherein said different pedestal delays produce device responses that occur within distinct, defined, separated time slots; and
(f) wherein the time slot in which each device response occurs provides a means to identify which acoustic track produced each response.

14. A surface acoustic wave film deposition monitoring and analysis device, comprising:
(a) A surface acoustic wave film deposition monitoring and analysis device as in claim 11;
(b) further comprising at least three SAW elements in at least two of said at least three acoustic tracks;
(c) wherein said at least three SAW elements are arranged to produce at least two differential delay line responses;
(d) wherein the SAW elements in each of said at least three acoustic tracks operate at a set frequency, selected from a set of at least three distinct, defined, separated frequency ranges (or bands); and
(e) wherein the frequency band in which each device response occurs provides a means to identify which acoustic track produced each response.

15. A surface acoustic wave film deposition monitoring and analysis device, comprising:
(a) A surface acoustic wave film deposition monitoring and analysis device as in claim 11;
(b) further comprising at least three SAW elements in at least two of said at least three acoustic tracks;
(c) wherein the SAW elements in each of said at least three acoustic tracks operate at a set frequency, selected from a set of two or more distinct, defined, separated frequency ranges (or bands);
(d) wherein said at least three SAW elements are arranged to produce at least two differential delay line responses;
(e) further comprising at least two different pedestal acoustic delays;
(f) wherein said different pedestal delays produce device responses that occur within distinct, defined, separated time slots; and
(g) wherein the combination of the frequency band and the time slot in which each device response occurs provides a means to identify which acoustic track produced each response.

16. A set of individually identifiable surface acoustic wave film deposition monitoring and analysis devices, comprising:
(a) at least two surface acoustic wave film deposition monitoring and analysis devices as in claim 11;
(b) each of said at least two surface acoustic wave film deposition monitoring and analysis devices further comprising different pedestal acoustic delays;
(c) wherein said different pedestal delays produce device responses that occur within distinct, defined, separated time slots; and
(d) wherein the time slot in which each device response occurs provides a means to identify each device.

17. A set of individually identifiable surface acoustic wave film deposition monitoring and analysis devices, comprising:
(a) at least two surface acoustic wave film deposition monitoring and analysis devices as in claim 11;
(b) each of said at least two surface acoustic wave film deposition monitoring and analysis devices further comprising different operating frequencies;
(c) wherein said different operating frequencies produce device responses that occur within distinct, defined, separated frequency bands; and
(d) wherein the frequency band in which each device response occurs provides a means to identify each device.

18. A set of individually identifiable surface acoustic wave film deposition monitoring and analysis devices, comprising:
(a) at least three surface acoustic wave film deposition monitoring and analysis devices as in claim 11;
(b) at least two of said at least three surface acoustic wave film deposition monitoring and analysis devices further comprising different operating frequencies, selected from a set of two or more distinct, defined, separated frequency ranges (or bands); and
(c) at least two of said at least three surface acoustic wave film deposition monitoring and analysis devices further comprising different pedestal acoustic delays;
(d) wherein said different pedestal delays produce device responses that occur within distinct, defined, separated time slots; and
(e) wherein said different operating frequencies produce device responses that occur within distinct, defined, separated frequency bands; and
(f) wherein the combination of the frequency band and the time slot in which each device response occurs provides a means to identify each device.

19. A set of individually identifiable surface acoustic wave notch devices, as described in claim 18, wherein the combination of the frequency band and the time slot in which each device response occurs provides a means to identify which device and acoustic track produced each response.

20. A surface acoustic wave notch device, comprising
(a) a piezoelectric substrate;
(b) at least one first transducer arranged on at least a portion of said piezoelectric substrate wherein said first transducer has electrode structures so as to be capable of generating and receiving acoustic waves at desired frequencies, and wherein said first transducer has an impulse response time duration of td1;
(c) at least one second surface acoustic wave element formed on said piezoelectric substrate and spaced from said first transducer along the direction of acoustic wave propagation at a distance to create a first acoustic delay, said at least one second surface acoustic wave element comprising electrode structures capable of interacting with acoustic waves at frequencies that correspond to the frequencies generated by said first transducer, and wherein said second SAW element has an impulse response time duration of td2;
(d) at least one third surface acoustic wave element formed on said piezoelectric substrate and spaced from said first transducer along the direction of acoustic wave propagation at a distance to create a second acoustic delay, said at least one second surface acoustic wave element comprising electrode structures capable of interacting with acoustic waves at frequencies that correspond to the frequencies generated by said first transducer, and wherein said third SAW element has an impulse response time duration of td3;
(e) wherein said second and third acoustic wave elements interact with the acoustic wave launched by said first transducer to produce first and second signals occurring at first and second acoustic delays, $t_1$ and $t_2$, respectively;
(f) wherein the time duration TD1 of the first signal produced through application of an impulse to said first transducer, and as a result of the acoustic wave generated by said impulse interacting with said first transducer and said second SAW element, is equal to at least the sum of the time duration of the impulse response of said first transducer (td1) plus the time duration of the impulse response of said second SAW element (td2) (TD1≥td1+td2);
(g) wherein the time duration TD2 of the second signal produced through application of an impulse to said first transducer, and as a result of the acoustic wave generated by said impulse interacting with said first transducer and said third SAW element, is equal to at least the sum of the time duration of the impulse response of said first transducer (td1) plus the time duration of the impulse response of said third SAW element (td3) (TD2≥td1+td3);
(h) wherein said first and second delays $t_1$ and $t_2$ are unequal, causing a separation $\Delta t=|t_1-t_2|$ between the centers of said first and second signals;
(i) wherein the durations TD1 and TD2 of said first and second signals are longer than said separation $\Delta t$, such that said first and second signals overlap in time; and
(j) wherein the combined response of said first and second signals effect a composite impulse response signal comprising a bandpass filter response with one or more notches (also known as nulls) in the frequency domain response.

21. A surface acoustic wave notch device, comprising:
(a) A surface acoustic wave notch device as in claim 20;
(b) further comprising at least two acoustic tracks, each containing at least two SAW elements, at least one of which is a transducer;
(c) wherein at least one of said at least two acoustic tracks is protected from exposure to environmental factors other than temperature; and
(d) wherein at least one of said at least two acoustic tracks has a portion of the acoustic wave propagation path exposed to environmental factors.

22. A surface acoustic wave notch device, comprising:
(a) A surface acoustic wave notch device as in claim 20;
(b) further comprising at least three acoustic tracks, each containing at least two SAW elements, at least one of which is a transducer;
(c) wherein at least one of said at least three acoustic tracks is protected from exposure to environmental factors other than temperature;
(d) wherein at least one of said at least three acoustic tracks has a portion of the acoustic wave propagation path exposed to environmental factors; and
(e) wherein at least one of said at least three acoustic tracks has a portion of the acoustic wave propagation path both coated with a conductive material and exposed to environmental factors.

23. A set of individually identifiable surface acoustic wave notch devices, comprising:
(a) A at least two surface acoustic wave notch devices as in claim 20;
(b) each of said at least two notch devices further comprising different pedestal acoustic delays;
(c) wherein said different pedestal delays produce device responses that occur within distinct, defined, separated time slots; and
(d) wherein the time slot in which each device response occurs provides a means to identify each device.

24. A set of individually identifiable surface acoustic wave notch devices, comprising:
(a) A at least two surface acoustic wave notch devices as in claim 20;
(b) each of said at least two notch devices further comprising different operating frequencies;
(c) wherein said different operating frequencies produce device responses that occur within distinct, defined, separated frequency bands; and (d) wherein the frequency band in which each device response occurs provides a means to identify each device.

25. A surface acoustic wave notch sensor device, comprising:
(a) A surface acoustic wave notch devices as in claim 20;
(b) further comprising at least two acoustic channels to effect measurement of temperature in addition to measurement of the film being deposited or the surface reaction or modification being sensed.

26. A surface acoustic wave notch device, comprising:
(a) A surface acoustic wave notch device as in claim 20;
(b) wherein said at least two acoustic channels may include different nominal first and second acoustic delays;
(c) and wherein said at least two acoustic channels may include different values of |first acoustic delay−second acoustic delay|.

27. A surface acoustic wave film deposition monitoring and analysis device, comprising:
(a) A surface acoustic wave film deposition monitoring and analysis device as in claim 6;
(b) wherein said at least two acoustic channels may include different nominal first and second acoustic delays;
(c) and wherein said at least two acoustic channels may include different values of |first acoustic delay−second acoustic delay|.

* * * * *